United States Patent [19]

Shimizu

[11] Patent Number: 5,707,972
[45] Date of Patent: Jan. 13, 1998

[54] HYDROPHILIC POLYSACCHARIDE-BASED PHARMACEUTICAL PERPARATION FOR EXTERNAL USE

[75] Inventor: Hideki Shimizu, Onomichi, Japan

[73] Assignee: Shimizu Chemical Corporation, Hiroshima-ken, Japan

[21] Appl. No.: 610,965

[22] Filed: Mar. 5, 1996

[51] Int. Cl.$^6$ .................. A61K 31/715; A61K 31/74; C08B 37/00

[52] U.S. Cl. .................. 514/54; 514/53; 536/114; 424/78.06

[58] Field of Search .................. 514/53, 54; 536/114; 424/78.06

[56] References Cited

U.S. PATENT DOCUMENTS 5,169,639  12/1992  Baichwal et al. .................. 424/468
5,206,159   4/1993  Samain et al. .................. 435/101
5,446,070   8/1995  Mantelle .................. 424/485

*Primary Examiner*—John Kight
*Assistant Examiner*—Everett White
*Attorney, Agent, or Firm*—Millen, White, Zelano, & Branigan, P.C.

[57] ABSTRACT

The present invention provides a pharmaceutical preparation for the treatment of a wound consisting essentially of 200-mesh or finer powder of one or more hydrophilic polysaccharides selected from the group consisting of glucomannan and guar gum. Also provided is a pharmaceutical preparation for prophylaxis and treatment of chapped skin consisting essentially of an aqueous solution of one or more hydrophilic polysaccharides selected from the group consisting of glucomannan and guar gum.

16 Claims, No Drawings

HYDROPHILIC POLYSACCHARIDE-BASED PHARMACEUTICAL PERPARATION FOR EXTERNAL USE

FIELD OF THE INVENTION

The present invention relates to pharmaceutical preparations for external use which comprise one ore more hydrophilic polysaccharides. More specifically, the present invention relates to pharmaceutical preparations for external use for hemostasis and treatment of simple as well as inflamed wounds in the skin which preparations comprise one ore more hydrophilic polysaccharides in powder form, and to pharmaceutical preparations for external use for prophylaxis and treatment of chapped skin which preparations comprise an aqueous solution of one or more hydrophilic polysaccharides.

BACKGROUND OF THE INVENTION

It is known to apply an ointment or an adhesive plaster to a skin wound in order to stop bleeding or to promote healing of the wound, whether it is a simple, suppurative or inflamed wound. Where the wound is bleeding, quick hemostasis is important for a speedy healing of the wound. After hemostasis, it is also important to effectively remove such exudates as plasma and pus from the wound so as to dry the affected site to eliminate bacteria and prevent their growth within the wound, as well as to avoid additional infection with bacteria coming from outer environment. However, either an ointment or an adhesive plaster is incapable of sufficiently removing exudates from the wound.

In addition, as an ointment layer applied over the wound has substantial fluidity, it is impossible for the layer to provide a tight cover to the wound needed for its isolation from outer environment, and, thus, application of ointment is useless for blocking bacterial ingress from outer environment to the wound surface. Likewise, an adhesive plaster does not have a function of isolating the wound from outer environment.

Upon this background, JP-B-57-1266 discloses pharmaceutical preparations for external use which comprise dried spherical polymer particles comprised of cross-linked dextran or cross-linked carboxymethyl dextran and the like. The preparations has property of absorbing such exudates as plasma from the wound and thereby swelling.

However, in the preparations disclosed in the JP-B-57-1266, the spherical polymer particles remain unbound with each other in the covering layer even after their swelling by absorption of exudates from the wound. Thus, the covering layer thus formed is quite fragile so that it can be readily wiped off with a spatula as described in JP-B-57-1266. Therefore, when the preparation is applied to a wound located on the surface of the body, there is a considerable risk that, due to body movements or an inadvertently applied impact on the wound, the covering layer may be partly torn open or detached from the wound, resulting in exposure of the wound surface to the outer environment. Such exposure, if it occurred, would impose a risk of infection with bacteria coming from outer environment. If the wound is infected with bacteria resistant to therapy, the infection might lead to a critical situation. Therefore, it is highly important that the integrity of the covering layer over the wound be maintained during the course of healing.

Thus, an object of the present invention is to provide a pharmaceutical preparation which, contrary to the prior preparations such as those described in JP-B-57-1266, forms a sufficiently tight, essentially amorphous layer over the wound through absorption of such exudates as blood, plasma and pus.

It is another object of the present invention to provide a method of treatment for skin wounds in a human utilizing such a pharmaceutical preparation.

It is still another object of the present invention to provide a pharmaceutical preparation and a method for prophylaxis and treatment of chapped skin.

SUMMARY OF THE INVENTION

Thus, one aspect of the present invention provides pharmaceutical preparations for external use consisting essentially of a powder of one or more hydrophilic polysaccharides such as, but not limited to, glucomannan and guar gum.

Hydrophilic polysaccharides such as glucomannan and guar gum can absorb a large amount of water per their unit amount. They thus are capable of quickly and sufficiently absorbing such exudates as blood, plasma and pus from a wound in the skin. Those substances can thus dry up the wound and thereby promote healing and, in addition, can also act to stop bleeding from the wound, allowing for a speedy healing.

Moreover, these hydrophilic polysaccharide particles have a property to swell upon absorption of exudates from a wound and make a thick paste, forming a very tight, essentially amorphous covering layer over the surface of the wound. Due to this tight covering layer, invasion of bacteria from outer environment is prevented, and penetration of air from outside also nearly completely blocked. Unlike the particles in JP-B-57-1266, which form a layer through their simple aggregation with each other, the layer formed by the swelling of hydrophilic polysaccharide particles of the present invention is of a substantially amorphous consistency such as a paste, being much more tougher than the layer formed from the prior art preparation, i.e., the layer in accordance with the present invention is much less likely to be torn or detached from the wound upon body motion or due to an inadvertent impact.

Thus, the integrity of the covering layer is more likely to be maintained and the risk of bacterial infection from outside will be minimized.

In addition, these hydrophilic polysaccharides do not possess any irritating nature to a skin wound, causing no undesirable effect on the wound even after a prolonged contact.

When it is applied to a suppurative wound, the strongly water absorbing preparation of the present invention absorbs exudates and dries up the wound. Thus, the healing of the wound is promoted and secondary infection prevented by the tight layer made from the preparation.

Moreover, due to their notable hydrophilicity, the layer formed of these compounds can be quite easily removed from the wound by simple washing with physiological saline, when required.

Thus, in an aspect of the present invention, a method is provided for the treatment of a skin wound of a human comprising spreading over the opening of the wound a therapeutically effective amount of a pharmaceutical preparation consisting essentially of one or more powder form hydrophilic polysaccharides selected from the group consisting of glucomannan and guar gum.

Another aspect of the present invention provides pharmaceutical preparations for external use consisting essentially of an aqueous solution of one or more hydrophilic polysaccharides such as, but not restrictive to, glucomannan and guar gum.

For the treatment of chapped skin, the aqueous preparation of the present invention will be applied to the affected area of the skin. When applied to a chapped area of the skin, the one or more polysaccharides in the preparation provide a tight amorphous coating layer over the chapped area and protect the site from outer stimuli, thereby allowing speedy healing of the chapped skin. In addition, the aqueous preparation of the present invention is useful for prophylaxis of skin chapping. For instance, chapping of hand skin due to the use of detergents will be prevented by a tight amorphous coating layer on the skin surface provided by the aqueous preparation applied after the use of the detergent.

Thus, in still another aspect of the present invention, a method is provided for the prophylaxis and treatment of chapped skin of a human comprising applying to the skin area to be protected against or treated for chapping a prophylactically or therapeutically effective amount of a pharmaceutical preparation consisting essentially of an aqueous solution obtainable by dissolving in water one or more hydrophilic polysaccharides selected from the group consisting of glucomannan and guar gum.

DETAILED DESCRIPTION

In one embodiment, the preparation of the present invention consists of one or more hydrophilic polysaccharides.

In another embodiment, the preparation of the present invention comprises one or more hydrophilic polysaccharides and one ore more externally usable, pharmacologically active compounds uniformly dispersed in powder form. Examples of such active compounds include, but are not limited to, local anesthetics such as dibucaine hydrochloride, tetracaine hydrochloride and lidocaine hydrochloride, and antimicrobials including benzethonium chloride, benzalkonium chloride, chlorhexidine and its salts such as chlorhexidine dihydrochloride, chlorhexidine diacetate and chlorhexidine gluconate.

For direct application to the skin in powder form, 200-mesh or finer powder of the hydrophilic polysaccharides are preferred.

In use, when there is bleeding from the cut in the skin, the powder is spread over the opening of the wound. Due to their strong water absorptive power, a rapid coagulation of the blood is achieved, bleeding minimized, and thus scab formation will be made negligible. In addition, these polysaccharides also absorb the blood and thereby swell to form a tight layer which prevents ingress of bacteria. This, in turn, prevents suppuration of the wound and accelerate its healing. Once healed, the layer of polysaccharides will peel off spontaneously.

In still another embodiment of the present invention, a preparation is provided which consists essentially of an aqueous solution obtainable by dissolving one or more hydrophilic polysaccharides in water. Such a preparation is useful for prevention and/or treatment of chapped skin. Preferably, such an aqueous preparation is prepared by dissolving glucomannan or guar gum in water. The preferable particle sizes of such polysaccharides before mixing with water are 200-mesh or smaller. Such polysaccharides are preferably contained at a total concentration of 0.1 to 10.0 W/V %, and more preferably 0.5 to 2 W/V %. The aqueous preparation of the present invention may also contain preservatives including, but not limited to, p-hydroxybenzoate derivatives, benzalkonium chloride, chlorhexidine and its salts such as chlorhexidine dihydrochloride, chlorhexidine diacetate and chlorhexidine gluconate, keratin softening preparations such as, but not limited to, urea, and other skin care agents.

The healing promotive activity of the present preparations applied to bleeding wounds is demonstrated in the following experiment.

EXPERIMENT

Ten rabbits were randomly divided into two groups for test preparations A and B. At 10 a.m. in the first day of testing, the rabbits had their hairs cut in the back with a heir clipper. The right and the left parts of the skin area with cut hairs were used for the test. In group A, the right part was used for control and the left part for the preparation of the present invention. In group B, contrarily, the left part was used for control and the right part for the preparation of the present invention.

A 2.5 cm X 2.5 cm area in each of the two parts of the back skin was wiped with ethanol for disinfection and then cut by about 5 mm long with a sterilized scalpel to cause bleeding. The wound on the control side was immediately covered with a piece of sterile gauze of the size of 2.0 cm X 2.0 cm (avoiding sticking to the wound), which was secured to the skin using an adhesive plaster. The wound on the other side in ten animals was sprinkled with a sufficient amount of glucomannan powder (for 10 animals) or a guar gum powder (for 10 animals) having particle sizes not greater than 200-mesh. After hemostasis was obtained, the wound was covered with a piece of sterile gauze of the size of 2.0 cm X 2.0 cm, which was secured to the skin using an adhesive plaster.

After the operation, the wounds were visually inspected every morning at 10 a.m. for the course of healing. The gauze was exchanged for fresh sterile one after each inspection of the wound. The wounds were regarded to have healed on the day when the scab was found to have spontaneously peeled off. Tables 1 and 2 show the numbers of the wounds found to have healed for each day after the operation.

TABLE 1

| Healing days for Glucomannan treated wounds | | | | | | |
|---|---|---|---|---|---|---|
| | Healing day | | | | | Mean |
| | 1 | 2 | 3 | 4 | | healing day |
| No. of test wounds | 0 | 6 | 4 | 0 | (n = 10) | 2.4 |
| No. of control wounds | 0 | 2 | 6 | 2 | (n = 10) | 3.0 |

TABLE 2

| Healing days for Guar gum treated wounds | | | | | | |
|---|---|---|---|---|---|---|
| | Healing day | | | | | Mean |
| | 1 | 2 | 3 | 4 | | healing day |
| No. of test wounds | 0 | 5 | 5 | 0 | (n = 10) | 2.5 |
| No. of control wounds | 0 | 2 | 5 | 3 | (n = 10) | 3.1 |

The above results demonstrate that the hydrophilic polysaccharides, glucomannan and guar gum, promoted healing of the skin wounds.

EXAMPLES

Example 1 Powder Form Pharmaceutical Preparation

Glucomannan or guar gum with particle sizes of 200 mesh or smaller is prepared by a conventional grinding method and used as a pharmaceutical preparation for external use of the present invention.

Example 2 Powder Form Pharmaceutical Preparation

The following ingredients are mixed together by a conventional method to form a powder form pharmaceutical preparation for external use.

| | |
|---|---|
| Glucomannan or guar gum (200-mesh or smaller) | 99.8 g |
| Dibucaine hydrochloride | 0.1 g |
| Benzethonium chloride | 0.1 g |

Example 3 Aqueous Pharmaceutical Preparation

The following ingredients are mixed together to dissolve by a conventional method to form an aqueous pharmaceutical preparation for external use.

| | |
|---|---|
| Glucomannan or guar gum (200-mesh or smaller) | 5.0 g |
| Urea | 5.0 g |
| Parabens | 0.1 g |
| Water | total to 100 ml |

What is claimed is:

1. A pharmaceutical preparation for external use consisting essentially of one or more powder form hydrophilic polysaccharides and one or more local anesthetics and/or antimicrobials.

2. The pharmaceutical preparation of claim 1 wherein the one ore more powder form hydrophilic polysaccharides are selected from the group consisting of glucomannan and guar gum.

3. The pharmaceutical preparation or claim 2 wherein the particle sizes of the powder form hydrophilic polysaccharides are substantially 200-mesh or smaller.

4. The pharmaceutical preparation of claim 2 wherein the one or more antimicrobials are selected from the group consisting of benzethonium chloride, benzalkonium chloride, chlorhexidine, chlorhexidine dihydrochloride, chlorhexidine diacetate and chlorhexidine gluconate.

5. The pharmaceutical preparation of claim 1 wherein the one or more local anesthetics are selected from the group consisting of dibucaine hydrochloride, tetracaine hydrochloride and lidocaine hydrochloride.

6. A pharmaceutical preparation for external use consisting essentially of an aqueous solution of one or more hydrophilic polysaccharides and one or more preservatives and/or keratin softening preparations.

7. The pharmaceutical preparation of claim 6 wherein the one ore more hydrophilic polysaccharides are selected from the group consisting of glucomannan and guar gum.

8. The pharmaceutical preparation of claim 7 wherein the aqueous solution is obtainable by dissolving in water the one of more hydrophilic polysaccharides with substantial particle sizes of 200-mesh or smaller.

9. The pharmaceutical preparation of claim 8 wherein the total concentration of the one or more hydrophilic polysaccharides is 0.1 to 10.0 W/V %.

10. The pharmaceutical preparation of claim 8 wherein the one or more preservatives are selected from the group consisting of p-hydroxybenzoate derivatives, benzalkonium chloride, chlorhexidine, chlorhexidine dihydrochloride, chlorhexidine diacetate and chlorhexidine gluconate.

11. The pharmaceutical preparation of claim 8 wherein the keratin softening preparation is urea.

12. A method of treatment of a skin wound of a human comprising spreading over the opening of the wound a therapeutically effective amount of a pharmaceutical preparation consisting essentially of one or more powder form hydrophilic polysaccharides selected from the group consisting of glucomannan and guar gum.

13. The method of claim 12 wherein the particle sizes of the one or more powder form hydrophilic polysaccharides are substantially 200-mesh or smaller.

14. The method of claim 12 wherein the pharmaceutical preparation contains one or more local anesthetics and/or antimicrobials.

15. A method of prophylaxis and treatment of chapped skin of a human comprising applying to the skin area to be protected against or treated for chapping a prophylactically or therapeutically effective amount of a pharmaceutical preparation consisting essentially of an aqueous solution obtainable by dissolving in water one or more hydrophilic polysaccharides selected from the group consisting of glucomannan and guar gum at a total concentration of 0.1 to 10.0 W/V %.

16. The method of claim 15 wherein the preparation contains one or more preservatives and/or keratin softening preparations.

\* \* \* \* \*